(12) United States Patent
Zhou

(10) Patent No.: US 11,382,660 B2
(45) Date of Patent: Jul. 12, 2022

(54) SEAL RING PROTECTION PIECE USED FOR PUNCTURE OUTFIT, END SEAL ASSEMBLY AND PUNCTURE OUTFIT

(71) Applicant: Xing Zhou, Guangdong (CN)

(72) Inventor: Xing Zhou, Guangdong (CN)

( * ) Notice: Subject to any disclaimer, the term of this patent is extended or adjusted under 35 U.S.C. 154(b) by 517 days.

(21) Appl. No.: 16/609,985

(22) PCT Filed: Oct. 27, 2017

(86) PCT No.: PCT/CN2017/107958
§ 371 (c)(1),
(2) Date: Oct. 31, 2019

(87) PCT Pub. No.: WO2018/077226
PCT Pub. Date: May 3, 2018

(65) Prior Publication Data
US 2021/0275219 A1   Sep. 9, 2021

(30) Foreign Application Priority Data
Oct. 31, 2016 (CN) .......................... 201610971243.9

(51) Int. Cl.
*A61B 17/34* (2006.01)

(52) U.S. Cl.
CPC .. *A61B 17/3462* (2013.01); *A61B 2017/3464* (2013.01)

(58) Field of Classification Search
CPC ........ A61B 17/3462; A61B 2017/3464; A61B 17/34; A61B 17/3496; A61B 17/3498;
(Continued)

(56) References Cited

U.S. PATENT DOCUMENTS

| 5,603,702 A | * | 2/1997 | Smith ................ A61B 17/3462 |
| | | | 251/149.1 |
| 2005/0077689 A1 | * | 4/2005 | Hueil ................ A61B 17/3421 |
| | | | 277/628 |

(Continued)

FOREIGN PATENT DOCUMENTS

| CN | 104083195 A | 10/2014 |
| CN | 204671236 U | 9/2015 |

(Continued)

OTHER PUBLICATIONS

Zhou, Xing, International Search Report and Written Opinion, PCT/CN2017/107958, dated Jan. 29, 2018, 8 pgs.

*Primary Examiner* — Diane D Yabut
*Assistant Examiner* — Brigid K Byrd
(74) *Attorney, Agent, or Firm* — Morgan, Lewis & Bockius LLP

(57) ABSTRACT

A sealing ring protection sheet for a trocar of the present invention includes a positioning skirt, a support piece and a curved protection sheet. An upper end of the support piece is connected to an inner side of the positioning skirt, and a lower end of the support piece is connected to an upper end of the curved protection sheet. The curved protection sheet is of a curved and asymmetrical sheet-like structure, forming an easily deformable region and a protection region along two sides of a center line and its extension line of the positioning skirt separately. A left side and a right side of the curved protection sheet have different curvatures. The design of different curvatures of the left and right sides reduces resistance forces when various special-shaped instruments are inserted and removed. An end sealing assembly and the trocar of the present invention include the sealing ring protection sheet for a trocar of the present invention, capable of not only ensuring that a funnel-shaped sealing ring is not punctured by a surgical instrument in a (Continued)

surgical process, thereby ensuring a good sealing performance, but also reducing a moving resistance force, and particularly reducing a resistance force when various special-shaped surgical instruments are inserted and removed.

18 Claims, 6 Drawing Sheets

(58) Field of Classification Search
CPC .. A61B 17/00234; A61B 17/3417–2017/3419; A61B 17/3423
See application file for complete search history.

(56) References Cited

U.S. PATENT DOCUMENTS

| | | | |
|---|---|---|---|
| 2005/0131349 A1 | 6/2005 | Albrecht et al. | |
| 2007/0185453 A1* | 8/2007 | Michael ............ | A61B 17/3462 604/164.01 |
| 2009/0270817 A1* | 10/2009 | Moreno ............ | A61B 17/3462 604/264 |
| 2010/0228091 A1* | 9/2010 | Widenhouse ...... | A61B 17/0218 600/203 |
| 2015/0223833 A1 | 8/2015 | Coffeen et al. | |

FOREIGN PATENT DOCUMENTS

| | | |
|---|---|---|
| CN | 105615954 A | 6/2016 |
| CN | 105662545 A | 6/2016 |
| CN | 206675578 U | 11/2017 |

* cited by examiner

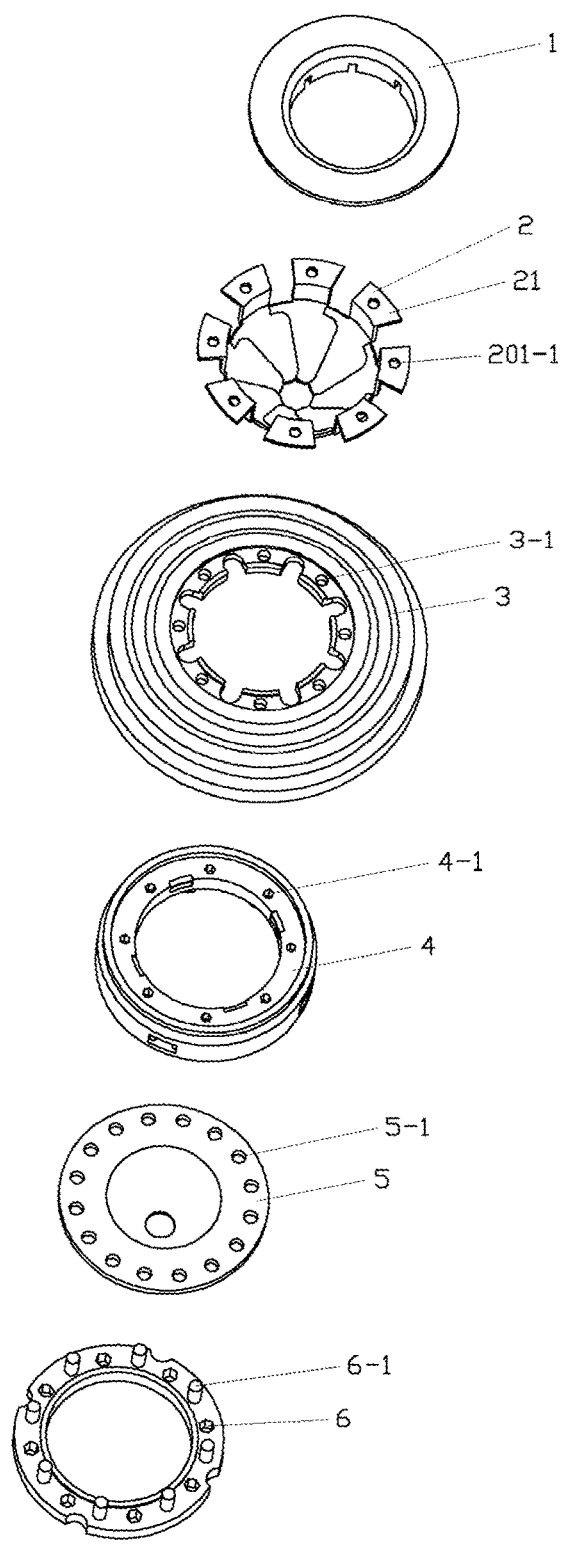
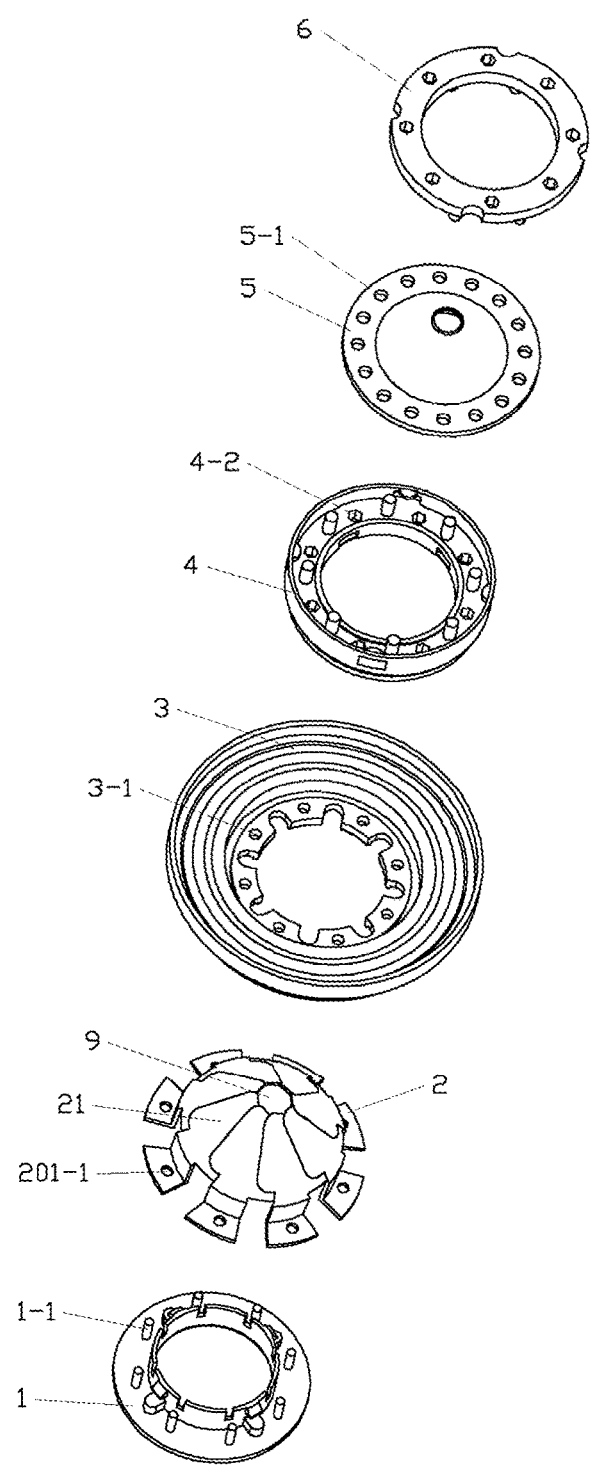
FIG. 4-6                FIG. 4-7

US 11,382,660 B2

SEAL RING PROTECTION PIECE USED FOR PUNCTURE OUTFIT, END SEAL ASSEMBLY AND PUNCTURE OUTFIT

CROSS REFERENCE TO RELATED APPLICATIONS

This Application is a United States National Stage Application filed under 35 U.S.C. § 371 of PCT Patent Application Serial No. PCT/CN2017/107958 filed on Oct. 27, 2017, which claims the benefit of and priority to Chinese Patent Application No. 201610971243.9 filed on Oct. 31, 2016, which are hereby incorporated by reference in their entirety.

FIELD OF THE INVENTION

The present invention relates to a surgical instrument, and in particular, to a sealing ring protection sheet for a trocar, an end sealing assembly and a trocar used in a laparoscopic surgery.

BACKGROUND OF THE INVENTION

Laparoscopic surgeries have been more widely applied. In order to avoid iatrogenic infection, consumption of disposable trocars (Trocar) used in laparoscopic surgeries is increasingly greater. To ensure a dynamic sealing of the trocar in a process that a surgical instrument is inserted and removed frequently is a key to ensure smooth operating of a surgery. Further, surgical instruments of different shapes may be used during the surgery. Therefore, the trocar further needs to be applicable to the surgical instruments of different shapes to facilitate insertion and removal of the instruments. In addition, a low resistance force needs to be maintained in the process of the insertion and removal of the instruments, so that a smooth operation of the instruments is guaranteed.

In a prior art, a universal radical sealing ring is a funnel-shaped sealing ring. In order to ensure that the sealing ring is not punctured by a surgical instrument in a long-term surgical process to cause a leakage, usually a sealing ring protection sheet is mounted on an upper portion of the funnel-shaped sealing ring, so that an instrument moves inwardly through the radial sealing ring along a surface of the protection sheet when the instrument is inserted in and removed from the trocar. A design of the sealing ring protection sheet, a thickness of the sealing ring can be reduced as much as possible while a sealing performance is kept, so that a resistance force of the sealing ring against insertion and removal of the instrument is reduced. However, the sealing ring protection sheet increases a moving resistance force on the insertion and removal of the instrument, vice versa. Particularly, for a special-shaped surgical instrument, such as a 7-shaped plier, or a surgical instrument with a raised step or a recess, the protection sheet of the prior art may be embedded in the raised step or the recess, creating a relatively great resistance force when the surgical instrument is inserted or removed. Therefore, the existing sealing ring protection sheet needs to be improved, to further reduce the moving resistance force of the protection sheet on the insertion and removal of the instrument while providing sufficient protection for the sealing ring.

SUMMARY

A sealing ring protection sheet for a trocar of the present invention is characterized in that: the sealing ring protection sheet 2 for a trocar includes a positioning skirt 201, a support piece 202 and a curved protection sheet 203;

A. the positioning skirt 201 is of a sheet-like structure, a positioning hole 201-1 being provided in the positioning skirt 201 and an inner side of the positioning skirt 201 being connected to an upper end of the support piece 202;

B. the support piece 202 is of a sheet-like structure, the upper end of the support piece 202 being connected to the inner side of the positioning skirt 201 and a lower end of the support piece 202 being connected to an upper end of the curved protection sheet 203; and C. the curved protection sheet 203 is of a curved and asymmetrical sheet-like structure, including a right bevel edge 203-1, a bottom edge 203-2, a left bevel edge 203-3, an upper edge 203-4 and a transition arc 203-23, the right bevel edge 203-1 and the left bevel edge 203-3 being at two sides of the bottom edge 203-2, the curved protection sheet 203 being suspended on the support piece 202, and the upper edge 203-4 of the curved protection sheet 203 being connected to a lower end of the support piece 202.

An included angle α between the curved protection sheet 203 and the support piece 202 is greater than or equal to 90°, usually between 90° and 170°.

An included angle β between the right bevel edge 203-1 and the bottom edge 203-2 is between 70° and 90°.

The right bevel edge 203-1 and the left bevel edge 203-3 are asymmetrically distributed along a center line and its extension line 203-0 of the positioning skirt 201.

A furthest distance D1 between the right bevel edge 203-1 and the center line and its extension line 203-0 of the positioning skirt 201 is less than a furthest distance D2 between the left bevel edge 203-3 and the center line and its extension line 203-0 of the positioning skirt 201.

The curved protection sheet 203 of the sealing ring protection sheet 2 for a trocar is disposed with an easily deformable region R with a relatively weak deformation strength and a protection region Q with a relatively strong deformation strength, and a deformation resistance force of the easily deformable region R is less than a deformation resistance force of the protection region Q.

The easily deformable region R is disposed on a right side of the curved protection sheet 203 of the sealing ring protection sheet 2 for a trocar, and the protection region Q is disposed on a left side of the curved protection sheet 203 of the sealing ring protection sheet 2.

A thickness of the easily deformable region R is less than a thickness of the protection region Q. Because the thickness of the easily deformable region R is less than that of the protection region Q, when an external force is applied, the easily deformable region R may be rapidly deformed prior to the protection region Q and retreat backwards, so that a moving resistance force on an instrument applied by the sealing ring protection sheet 2 for a trocar is reduced. The protection region Q can still well protect the funnel-shaped sealing ring 5, so as to avoid a leakage caused by that the funnel-shaped sealing ring 5 is punctured.

Because the curved protection sheet 203 adopts a curved and asymmetrical sheet-like structure, and is divided along the center line and its extension line 203-0 of the positioning skirt 201, the curved protection sheet 203 may form the easily deformable region R and the protection region Q separately on two sides of the center line and its extension line 203-0. According to description of the accompanying drawings of this application, a right side portion of the curved protection sheet 203 is the easily deformable region R, and a left side of the curved protection sheet 203 is the protection region Q. When a surgical instrument is inserted and removed, the region R is rapidly deformed under a force to rapidly expand a surgical instrument passage 9, and reduce a resistance force when the surgical instrument goes through the sealing ring protection sheet 2 for a trocar. After the region Q is slightly deformed, the region Q is still well fitted to the funnel-shaped sealing ring 5, so as to well protect the funnel-shaped sealing ring 5. By the design of the asymmetrical sheet-like structure of the curved protection sheet 203, not only the surgical instrument passage 9 can be rapidly opened to reduce the resistance force when the surgical instrument goes through, but also that the funnel-shaped sealing ring 5 is well protected, to ensure that the funnel-shaped sealing ring 5 is not easy to be punctured by the surgical instrument in a surgical process, thereby well meeting requirements of a protection function and a low moving resistance force on the sealing ring protection sheet 2 for a trocar.

A funnel-shaped protection sheet assembly 21 is formed by alternately stacking four or more sealing ring protection sheets 2 for the trocar.

Further, the funnel-shaped protection sheet assembly 21 is formed by alternately stacking eight sealing ring protection sheets 2 for the trocar at 45°. By alternately stacking the eight sealing ring protection sheets 2 for the trocar at 45°, a symmetrically distributed funnel-shaped structure with a good fitting effect may be well formed on an upper portion of the funnel-shaped sealing ring 5. By such the structure, when the surgical instrument goes through, an area of contact between the surgical instrument and the sealing ring 5 is reduced as much as possible due to the funnel-shaped protection sheet assembly 21 formed by alternately stacking the eight sealing ring protection sheets 2, and therefore a frictional resistance force of a motion of the instrument is reduced as much as possible while a sealing performance is guaranteed. This funnel-shaped protection sheet assembly 21 formed by the eight sealing ring protection sheets 2 is an optimal structure obtained through optimization.

A curvature of a left side portion of the curved protection sheet 203 is different from a curvature of a right side portion of the curved protection sheet 203.

Further, the curvature of the left side of the curved protection sheet 203 is less than the curvature of the right side of the curved protection sheet 203.

Because a radius of curvature of the right side of the curved protection sheet 203 is less than a radius of curvature of the left side of the curved protection sheet 203, that is, the curvature of the right side of the curved protection sheet 203 is greater than the curvature of the left side of the curved protection sheet 203, when a surgical instrument, especially, a special-shaped surgical instrument such as a 7-shaped plier or a surgical instrument with a raised step or a recess goes through, since the radius of curvature of the right side is smaller, the region R can be conveniently overturned during removal of the special-shaped surgical instrument due to the fact that the region R on the right side of the curved protection sheet 203 is small in a deformation resistance force, small in the radius of curvature and large in the curvature, thereby facilitating the removal of the special-shaped instrument and reducing a moving resistance force when the special-shaped instrument is removed, so that the sealing ring protection sheet 2 for a trocar is not apt to be clamped at a special-shaped part, such as a raised step or a recess and that a smoothness of insertion and removal of various special-shaped instruments is greatly improved.

An upper edge 203-4 of the curved protection sheet 203 includes a right-side upper edge 203-41, a left-side upper edge 203-42; and the right-side upper edge 203-41 is lower than the left-side upper edge 203-42. Therefore, when the surgical instrument goes through, the left-side upper edge 203-42 may not be deformed when a force is applied before the surgical instrument arrives at the right-side upper edge 203-41. When the surgical instrument arrives at the right-side upper edge 203-41, the region R on the right side of the curved protection sheet 203 is deformed rapidly, the region Q on the left side of the curved protection sheet 203 is deformed slightly, the surgical instrument passage 9 expands rapidly, and the surgical instrument enters the funnel-shaped sealing ring 5 after going through the sealing ring protection sheet 2 for a trocar. The right-side upper edge 203-41 is lower than the left-side upper edge 203-42, ensuring that the region R on the right side of the curved protection sheet 203 is deformed prior to the region Q on the left side of the curved protection sheet 203 when the surgical instrument goes through, so that the moving resistance force generated when the surgical instrument goes through is reduced.

The positioning skirt 201 is perpendicular to the support piece 202.

An end sealing assembly of the present invention includes the sealing ring protection sheet 2 for a trocar.

The end sealing assembly 20 comprises an upper pressing plate 1, a protection sheet 2, a corrugation sealing ring 3, a positioning seat 4, a funnel-shaped sealing ring 5 and a lower pressing plate 6; eight protection sheets 2 are mounted on positioning posts 1-1 of the upper pressing plate 1 through positioning holes 201-1, so that for two adjacent protection sheets 2, a right side 203-1 of the curved protection sheet 203 always presses a left side 203-3 of a curved protection sheet 203 of the adjacent protection sheet 2, the right side 203-1 of the curved protection sheet 203 is always in an upper layer, and the left side 203-3 of the curved protection sheet 203 is always in a lower layer, to thus form a circular funnel-shaped protection sheet assembly 21 by alternately stacking the protection sheets in this manner; positioning holes 3-1 of the corrugation sealing ring 3 are sleeved on the positioning posts 1-1 of the upper pressing plate 1, and the circular funnel-shaped protection sheet assembly 21 is disposed between the corrugation sealing ring 3 and the upper pressing plate 1; the positioning seat 4 is provided with upper positioning holes 4-1 and lower positioning holes 4-2, the positioning posts 1-1 of the upper pressing plate 1 are embedded in the upper positioning holes 4-1 of the positioning seat 4, and the protection sheets 2 and the corrugation sealing ring 3 are sequentially disposed between the upper pressing plate 1 and the positioning seat 4; and the funnel-shaped sealing ring 5 is provided with positioning holes 5-1, the lower pressing plate 6 is disposed with positioning posts 6-1, the positioning posts 6-1 of the lower pressing plate 6 are embedded in the lower positioning holes 4-2 of the positioning seat 4 through the positioning holes 5-1 of the funnel-shaped sealing ring 5, and the funnel-shaped sealing ring 5 is disposed between the lower pressing plate 6 and the positioning seat 4.

Because the circular funnel-shaped protection sheet assembly 21 is adopted, the end sealing assembly 20 not only ensures that the funnel-shaped sealing ring 5 is not punctured by the surgical instrument in a surgical process, but also reduces a moving resistance force, thereby well ensuring a moving smoothness of the surgical instrument.

The trocar of the present invention includes the sealing ring protection sheet 2 for a trocar.

Further, the trocar 29 includes the end sealing assembly 20.

The sealing ring protection sheet for a trocar of the present invention includes a positioning skirt 201, a support piece 202 and a curved protection sheet 203. An upper end of the support piece 202 is connected to an inner side of the positioning skirt 201, and a lower end of the support piece 202 is connected to an upper end of the curved protection sheet 203. The curved protection sheet 203 is of a curved and asymmetrical sheet-like structure, and along left and right sides of the center line and its extension line 203-0 of the positioning skirt 201, the easily deformable region R and the protection region Q are formed separately. When a surgical instrument goes through, the region R is rapidly deformed to rapidly expand a surgical instrument passage 9, and reduce a resistance force generated when the surgical instrument goes through. The region Q is only slightly deformed, and still well protect the funnel-shaped sealing ring 5. The left and right sides of the curved protection sheet 203 have different curvatures. A design of different curvatures of the left side and the right side reduces a moving resistance force generated during insertion and removal of various special-shaped instruments. The trocar including the sealing ring protection sheet for a trocar of the present invention is capable of not only ensuring that the funnel-shaped sealing ring 5 is not punctured by a surgical instrument in a surgical process to ensure a good sealing performance, but also reducing a moving resistance force to ensure a moving smoothness of the surgical instrument.

BRIEF DESCRIPTION OF THE DRAWINGS

The aforementioned features and advantages of the invention as well as additional features and advantages thereof will be more clearly understood hereinafter as a result of a detailed description of preferred embodiments when taken in conjunction with the drawings.

FIG. 1-1 is an A-A cutaway view of FIG. 1;

FIG. 2-1 is a top view of FIG. 2;

FIG. 2-2 is a bottom view of FIG. 2;

FIG. 2-3 is a side view of FIG. 2;

FIG. 2-4 is a side view of FIG. 2;

FIG. 3 depicts a protection sheet assembly composed of 8 sealing ring protection sheets for a trocar according to the present invention;

FIG. 3-1 is an exploded view of FIG. 3;

FIG. 3-2 is a bottom view of FIG. 3;

FIG. 3-3 is an exploded view of FIG. 3-2;

FIG. 3-4 is a front view of FIG. 3;

FIG. 3-5 is a B-B cutaway view of FIG. 3;

FIG. 4 is a top view of an end sealing assembly according to the present invention;

FIG. 4-1 is a front view of FIG. 4;

FIG. 4-2 is a bottom view of FIG. 4-1;

FIG. 4-3 is a top-view schematic three-dimensional structural diagram of FIG. 4-1;

FIG. 4-4 is a bottom-view schematic three-dimensional structural diagram of FIG. 4-1;

FIG. 4-5 is a C-C cutaway view of FIG. 4;

FIG. 4-6 is a top-view exploded view of FIG. 4-1;

FIG. 4-7 is a bottom-view exploded view of FIG. 4-1; and

FIG. 5 is schematic structural diagram of a trocar according to the present invention.

In the foregoing accompanying drawings:

Figure 1:
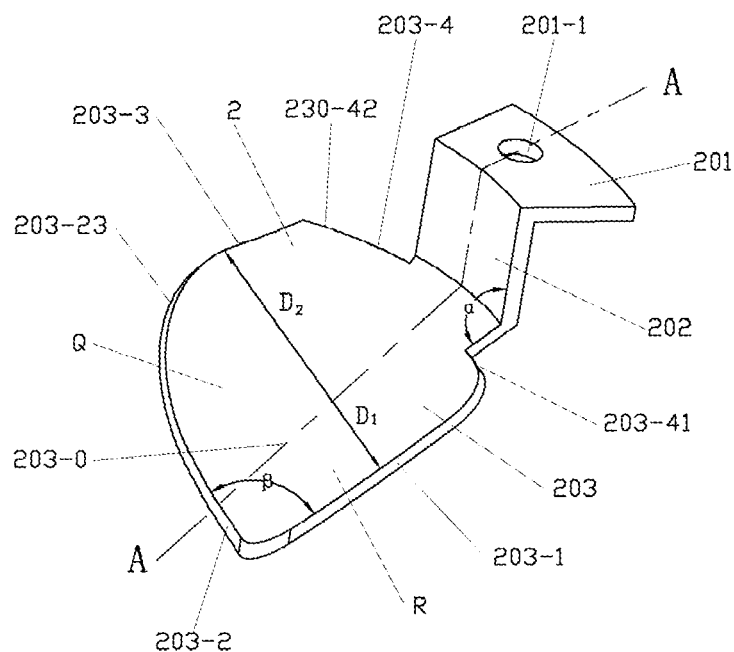
FIG. 1 is a schematic three-dimensional structural diagram of a sealing ring protection sheet for a trocar according to the present invention.

1 is an upper pressing plate, 2 is a sealing ring protection sheet for a trocar, 3 is a corrugation sealing ring, 4 is a positioning seat, 5 is a funnel-shaped sealing ring, 6 is a lower pressing plate, 9 is a surgical instrument passage, 20 is an end sealing assembly, 21 is a protection sheet assembly, and 29 is a trocar.

On the sealing ring protection sheet for a trocar:

201 is a positioning skirt, 202 is a support piece, and 203 is a curved protection sheet.

201-1 is a positioning hole.

203-0 is a center line and its extension line of the positioning skirt, 203-1 is a right bevel edge, 203-2 is a bottom edge, 203-3 is a left bevel edge, 203-4 is an upper edge, and 203-23 is a transition arc.

203-41 is a right-side upper edge of the upper edge of the curved protection sheet, and 203-42 is a left-side upper edge of the upper edge of the curved protection sheet.

A region R is an easily deformable region of the curved protection sheet, and a region Q is a protection region of the curved protection sheet.

$\alpha$ is an included angle between the curved protection sheet and the support piece, $\beta$ is an included angle between the right bevel edge and the bottom edge, D1 is a furthest distance between the right bevel edge and the center line and its extension line of the positioning skirt, and D2 is a furthest distance between the left bevel edge and the center line and its extension line of the positioning skirt.

On the end sealing assembly:

1-1 is a positioning post of the upper pressing plate, 3-1 is a positioning hole of the corrugation sealing ring, 4-1 is an upper positioning hole of the positioning seat, 4-2 is a lower positioning hole of the positioning seat, 5-1 is a positioning hole on the funnel-shaped sealing ring, and 6-1 is a positioning post on the lower pressing plate.

On the trocar:

100 is a sheath, and 200 is a penetration rod; 101 is an end cover, and 102 is a sheath assembly; 101-1 is an upper case, and 101-2 is a lower case.

Like reference numerals refer to corresponding parts throughout the several views of the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the subject matter presented herein. But it will be apparent to one skilled in the art that the subject matter may be practiced without these specific details. In other instances, well-known methods, procedures, components, and circuits have not been described in detail so as not to unnecessarily obscure aspects of the embodiments.

Embodiment 1: A Sealing Ring Protection Sheet for a Trocar of the Present Invention Refer to FIG. 1 to FIG. 3-5, in this embodiment, a sealing ring protection sheet 2 for a trocar includes a positioning skirt 201, a support piece 202 and a curved protection sheet 203.

The positioning skirt 201 is a sheet-like structure, and a positioning hole 201-1 is provided in the positioning skirt 201. An inner side of the positioning skirt 201 is connected to an upper end of the support piece 202. The positioning skirt 201 is perpendicular to the support piece 202.

The support piece 202 is of a sheet-like structure, the upper end of the support piece 202 being connected to the inner side of the positioning skirt 201 and a lower end of the support piece 202 being connected to an upper end of the curved protection sheet 203.

The curved protection sheet 203 is of a curved and asymmetrical sheet-like structure, including a right bevel edge 203-1, a bottom edge 203-2, a left bevel edge 203-3, an upper edge 203-4 and a transition arc 203-23. The right bevel edge 203-1 and the left bevel edge 203-3 are at two sides of the bottom edge 203-2, the curved protection sheet 203 is suspended on the support piece 202, and the upper edge 203-4 of the curved protection sheet 203 is connected to the lower end of the support piece 202.

An included angle α between the curved protection sheet 203 and the support piece 202 is greater than 90°. In this embodiment, the included angle α is between 120° and 170°.

An included angle β between the right bevel edge 203-1 and the bottom edge 203-2 is between 70° and 90°.

The right bevel edge 203-1 and the left bevel edge 203-3 are asymmetrically distributed along a center line and its extension line 203-0 of the positioning skirt 201.

A furthest distance D1 between the right bevel edge 203-1 and the center line and its extension line 203-0 of the positioning skirt 201 is less than a furthest distance D2 between the left bevel edge 203-3 and the center line and its extension line 203-0 of the positioning skirt 201.

The curved protection sheet 203 of the sealing ring protection sheet 2 for a trocar is disposed with an easily deformable region R with a relatively weak deformation strength and a protection region Q with a relatively strong deformation strength, and a deformation resistance force of the easily deformable region R is less than a deformation resistance force of the protection region Q.

The easily deformable region R is disposed on a right side of the curved protection sheet 203 of the sealing ring protection sheet 2 for a trocar, and the protection region Q is disposed on a left side of the curved protection sheet 203 of the sealing ring protection sheet 2.

A thickness of the easily deformable region R is less than a thickness of the protection region Q. Because the thickness of the easily deformable region R is less than that of the protection region Q, when an external force is applied, the easily deformable region R may be rapidly deformed prior to the protection region Q, and retreat backwards, so that a moving resistance force on an instrument applied by the sealing ring protection sheet 2 for a trocar is reduced. The protection region Q can still well protect the funnel-shaped sealing ring 5, so as to avoid a leakage caused by that the funnel-shaped sealing ring 5 is punctured.

Because the curved protection sheet 203 adopts a curved and asymmetrical sheet-like structure, and is divided along the center line and its extension line 203-0 of the positioning skirt 201, the curved protection sheet 203 may form the easily deformable region R and the protection region Q separately on two sides of the center line and its extension line 203-0. Refer to FIG. 1 and FIG. 1-1, a right side portion of the curved protection sheet 203 is the easily deformable region R, and a left side of the curved protection sheet 203 is the protection region Q. When a surgical instrument is inserted and removed, the region R is rapidly deformed under a force to rapidly expand a surgical instrument passage 9, and reduce a resistance force when the surgical instrument goes through the sealing ring protection sheet 2 for a trocar. After the region Q is slightly deformed, the region Q is still well fitted to the funnel-shaped sealing ring 5, so as to well protect the funnel-shaped sealing ring 5. By the design of the asymmetrical sheet-like structure of the curved protection sheet 203, not only the surgical instrument passage 9 can be rapidly opened to reduce the resistance force when the surgical instrument goes through, but also that the funnel-shaped sealing ring 5 is well protected, to ensure that the funnel-shaped sealing ring 5 is not easy to be punctured by the surgical instrument in a surgical process, thereby well meeting requirements of a protection function and a low moving resistance force on the sealing ring protection sheet 2 for a trocar.

Figure 2:
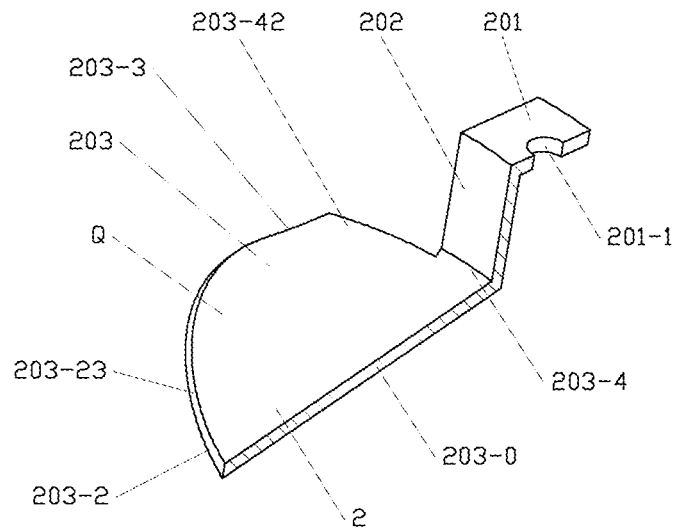
FIG. 2 is a front view of a sealing ring protection sheet for a trocar according to the present invention.
Figures 1, 2:
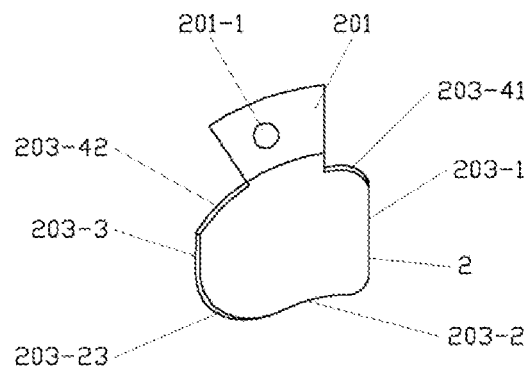
Figures 2, 3:
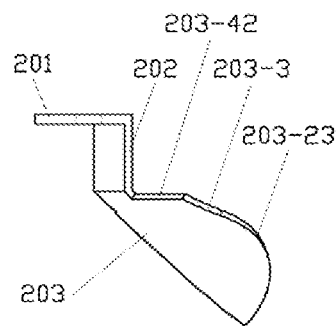
Figure 2:
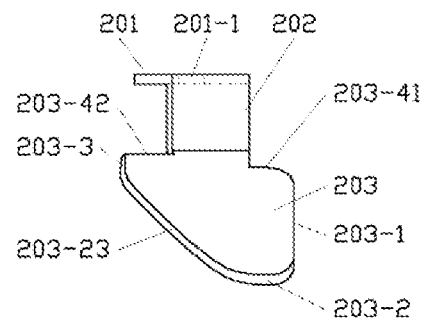
Figure 3:
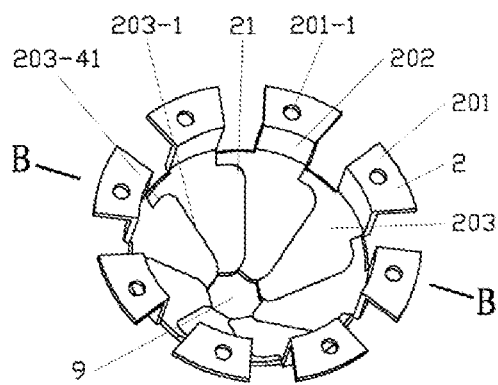
Figures 1, 3:
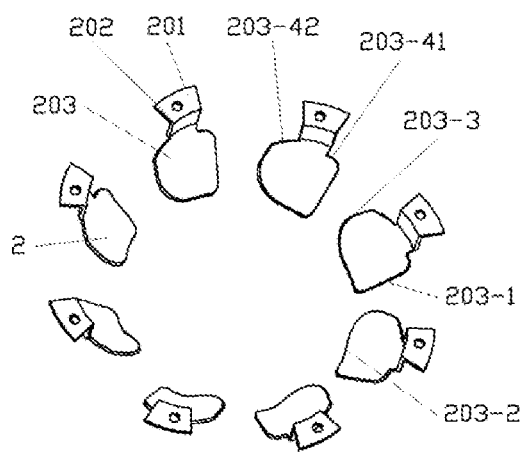
Figures 2, 3:
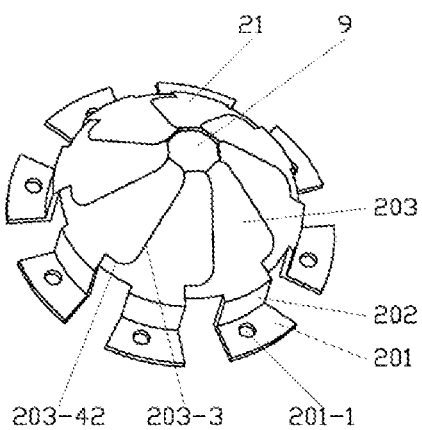
Figure 3:
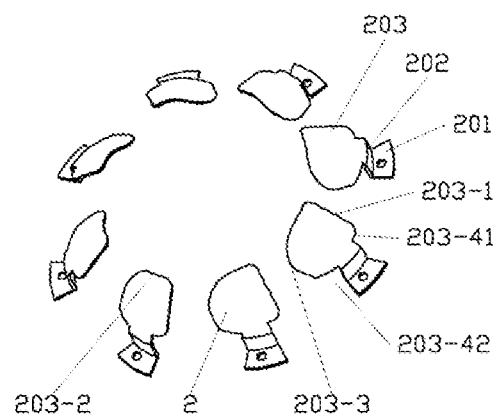
Figures 3, 4:
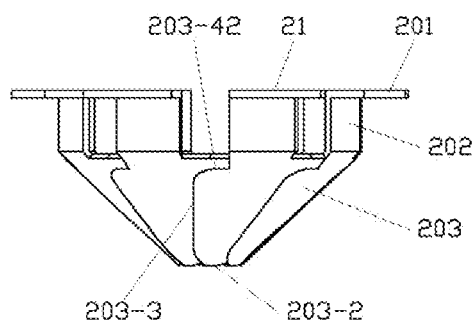
Figures 3, 4, 5:
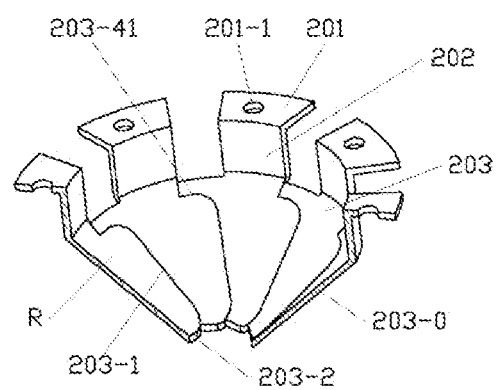
Figure 4:
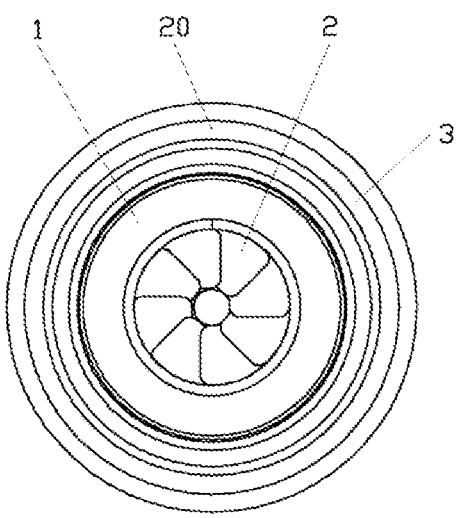
Figures 3, 4:
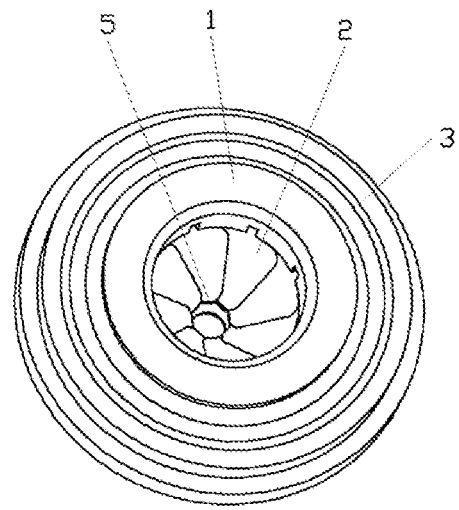
Figures 1, 4:
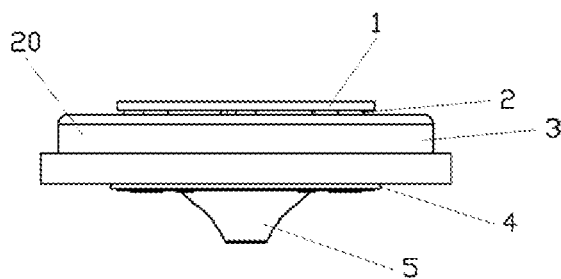
Figure 4:
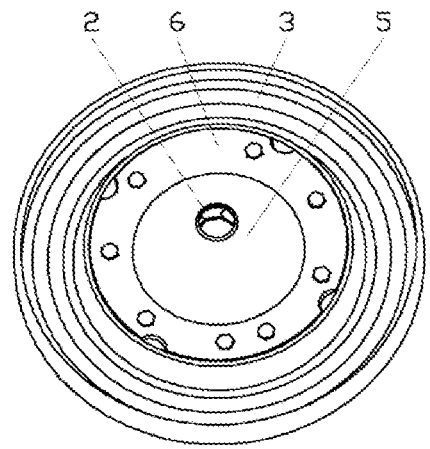
Figures 2, 4:
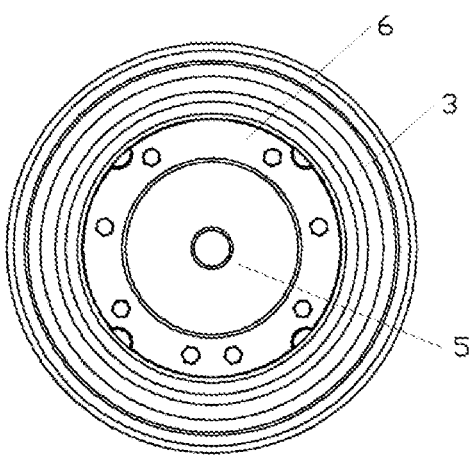
Figures 4, 5:
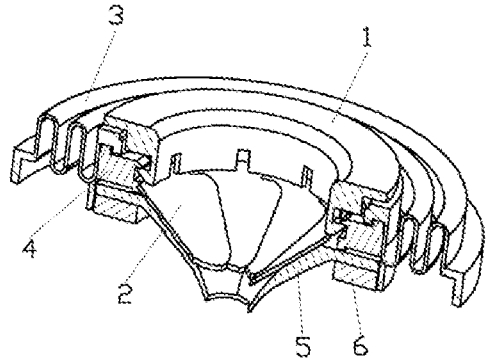
Figure 5:
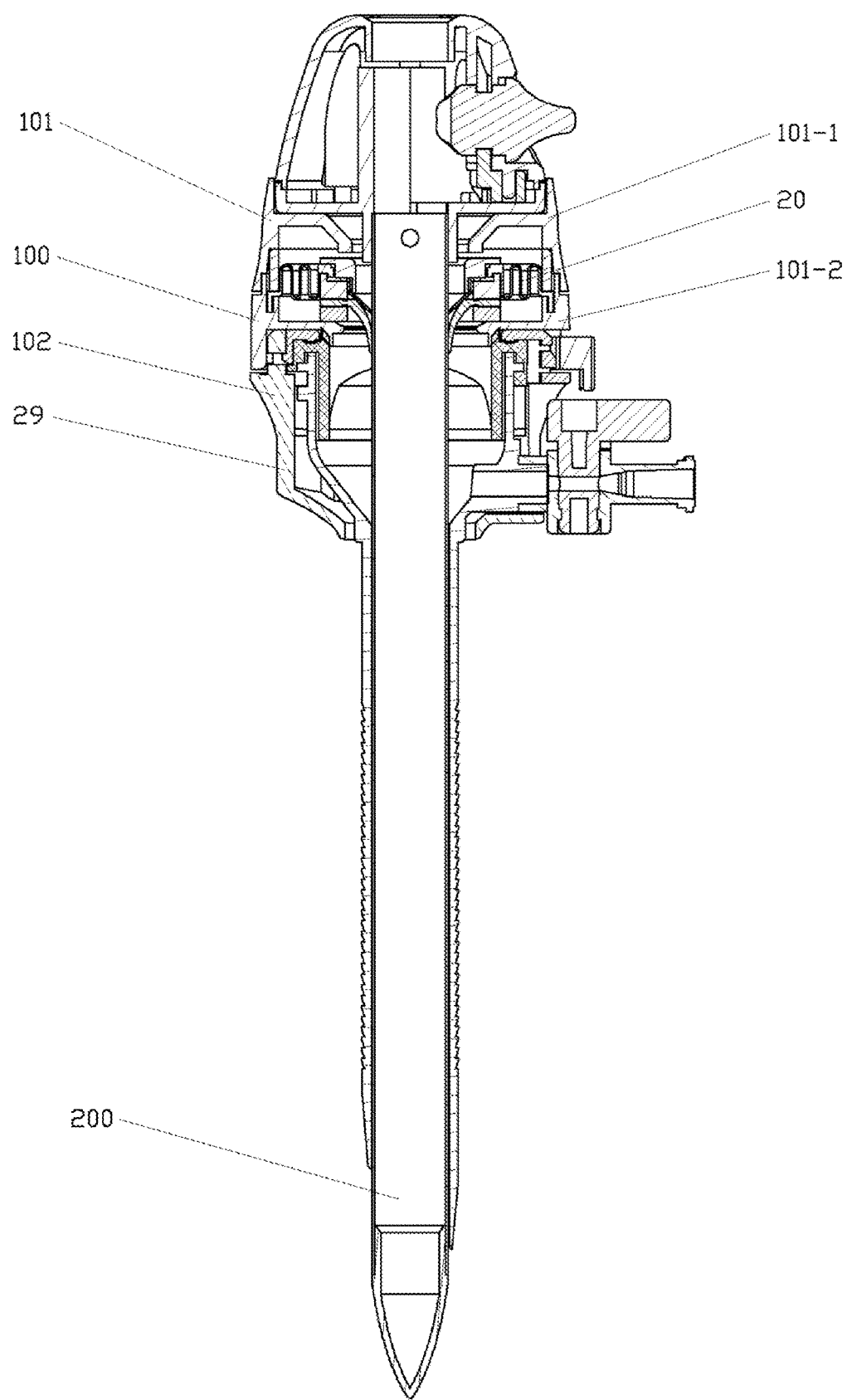

In this embodiment, the funnel-shaped protection sheet assembly 21 is formed by alternately stacking eight sealing ring protection sheets 2 for the trocar at 45°. Refer to FIG. 3 to FIG. 3-5. By alternately stacking the eight sealing ring protection sheets 2 for the trocar at 45°, a symmetrically distributed funnel-shaped structure with a good fitting effect may be well formed on an upper portion of the funnel-shaped sealing ring 5. By such the structure, when the surgical instrument goes through, an area of contact between the surgical instrument and the sealing ring 5 is reduced as much as possible due to the funnel-shaped protection sheet assembly 21 formed by alternately stacking the eight sealing ring protection sheets 2, and therefore a frictional resistance force of a motion of the instrument is reduced as much as possible while a sealing performance is guaranteed. This funnel-shaped protection sheet assembly 21 formed by the eight sealing ring protection sheets 2 is an optimal structure obtained through optimization.

A curvature of a left side portion of the curved protection sheet 203 is different from a curvature of a right side portion of the curved protection sheet 203.

Further, the curvature of the left side of the curved protection sheet 203 is less than the curvature of the right side of the curved protection sheet 203.

In this embodiment, a radius of curvature of the right side of the curved protection sheet 203 is 20 mm, a radius of curvature of the left side of the curved protection sheet 203 is 25 mm, and the radius of curvature of the right side of the curved protection sheet 203 is less than the radius of curvature of the left side of the curved protection sheet 203. That is, in this embodiment, the curvature of the right side of the curved protection sheet 203 is greater than the curvature of the left side of the curved protection sheet 203. Because a radius of curvature of the right side of the curved protection sheet 203 is less than a radius of curvature of the left side of the curved protection sheet 203, when a surgical instrument, especially, a special-shaped surgical instrument such as a 7-shaped plier or a surgical instrument with a raised step or a recess goes through, since the radius of curvature of the right side is smaller, the region R can be conveniently overturned during removal of the special-shaped surgical instrument due to the fact that the region R on the right side of the curved protection sheet 203 is small in a deformation resistance force, small in the radius of curvature and large in the curvature, thereby facilitating the removal of the special-shaped instrument and reducing a moving resistance force when the special-shaped instrument is removed, so that the sealing ring protection sheet 2 for a trocar is not apt to be clamped at a special-shaped part, such as a raised step or a recess and that a smoothness of insertion and removal of various special-shaped instruments is greatly improved.

An upper edge 203-4 of the curved protection sheet 203 includes a right-side upper edge 203-41, a left-side upper edge 203-42; and the right-side upper edge 203-41 is lower than the left-side upper edge 203-42. Therefore, when the surgical instrument goes through, the left-side upper edge 203-42 may not be deformed when a force is applied before the surgical instrument arrives at the right-side upper edge 203-41. When the surgical instrument arrives at the right-side upper edge 203-41, the region R on the right side of the curved protection sheet 203 is deformed rapidly, the region Q on the left side of the curved protection sheet 203 is deformed slightly, the surgical instrument passage 9 expands rapidly, and the surgical instrument enters the funnel-shaped sealing ring 5 after going through the sealing ring protection sheet 2 for a trocar. The right-side upper edge 203-41 is lower than the left-side upper edge 203-42, when the surgical instrument goes through, ensuring that the region R on the right side of the curved protection sheet 203 is deformed before the region Q on the left side of the curved protection sheet 203, so that the moving resistance force is reduced when the surgical instrument goes through.

An asymmetrical structural design of the curved protection sheet 203 not only ensures that the funnel-shaped sealing ring 5 is not punctured by the surgical instrument in a surgical process, but also reduces a moving resistance force, thereby well ensuring a moving smoothness of the surgical instrument.

Embodiment 2: An End Sealing Assembly of the Present Invention

Figures 2, 3, 4:
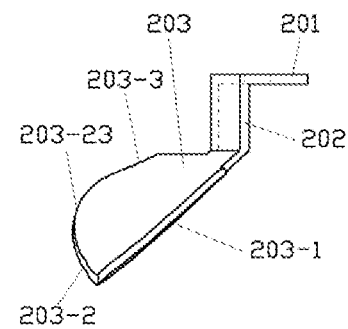
Figure 2:
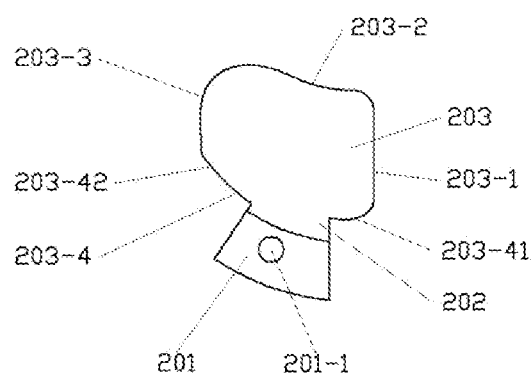

Refer to FIG. 4 to FIG. 4-7, an end sealing assembly of the present invention includes the sealing ring protection sheet 2 for a trocar of Embodiment 1, and a circular funnel-shaped protection sheet assembly 21 composed of the sealing ring protection sheets 2 for a trocar.

The end sealing assembly 20 includes an upper pressing plate 1, protection sheets 2, a corrugation sealing ring 3, a positioning seat 4, a funnel-shaped sealing ring 5 and a lower pressing plate 6. Refer to FIG. 4-6 and FIG. 4-7.

Eight protection sheets 2 are mounted on positioning posts 1-1 of the upper pressing plate 1 through positioning holes 201-1, so that for two adjacent protection sheets 2, a right side 203-1 of a curved protection sheet 203 always presses a left side 203-3 of a curved protection sheet 203 of the adjacent protection sheet 2, the right side 203-1 of the curved protection sheet 203 always is in an upper layer, and the left side 203-3 of the curved protection sheet 203 is always in a lower layer, to thus form the circular funnel-shaped protection sheet assembly 21 by alternately stacking the protection sheets in this manner. Refer to FIG. 3 to FIG. 3-5.

Positioning holes 3-1 of the corrugation sealing ring 3 are sleeved on the positioning posts 1-1 of the upper pressing plate 1, and the circular funnel-shaped protection sheet assembly 21 is disposed between the corrugation sealing ring 3 and the upper pressing plate 1. The positioning seat 4 is provided with upper positioning holes 4-1 and lower positioning holes 4-2, the positioning posts 1-1 of the upper pressing plate 1 are embedded in the upper positioning holes 4-1 of the positioning seat 4, and the protection sheet 2 and the corrugation sealing ring 3 are sequentially disposed between the upper pressing plate 1 and the positioning seat 4. The funnel-shaped sealing ring 5 is provided with positioning holes 5-1, the lower pressing plate 6 is disposed with positioning posts 6-1, the positioning posts 6-1 of the lower pressing plate 6 are embedded in lower positioning holes 4-2 of the positioning seat 4 through the positioning holes 5-1 of the funnel-shaped sealing ring 5, and the funnel-shaped sealing ring 5 is disposed between the lower pressing plate 6 and the positioning seat 4. Refer to FIG. 4 to FIG. 4-5.

Because the circular funnel-shaped protection sheet assembly 21 is adopted, the end sealing assembly 20 not only ensures that the funnel-shaped sealing ring 5 is not punctured by a surgical instrument in a surgical process, but also reduces a moving resistance force, well ensuring a smoothness of a insertion and removal of the surgical instrument, and particularly, benefiting insertion and removal of various special-shaped instruments.

Embodiment 3: A Trocar of the Present Invention

Refer to FIG. 5, in this embodiment, a trocar 29 includes the end sealing assembly 20 of Embodiment 2.

The trocar 29 includes a sheath 100 and a penetration rod 200. The sheath 100 includes an end cover 101 and a sheath assembly 102. The end sealing assembly 20 is embedded between an upper case 101-1 and a lower case 101-2 of the end cover 101.

Regardless of a structure of the penetration rod 200 and the sheath assembly 102, in this embodiment, a core of the trocar 29 lies in that the end sealing assembly 20 of the trocar 29 adopts the circular funnel-shaped protection sheet assembly 21 formed by alternately stacking the sealing ring protection sheets 2 of Embodiment 1.

The asymmetrical structural design of the curved protection sheet 203 of the sealing ring protection sheet 2 for a trocar not only ensures that the funnel-shaped sealing ring 5 is not punctured in a surgical process, but also reduces a moving resistance force of a surgical instrument, thereby well ensuring a moving smoothness of the surgical instrument, and particularly, benefiting insertion and removal of various special-shaped instruments, so that the trocar of the present invention has a good clinical use value.

It should be noted that, the structures disclosed and described in the present invention may be replaced with other structures of the same effect, and meanwhile embodiments of the present invention described herein are not the sole structure to implement the present invention. Although the preferred embodiments of the present invention have been introduced and described in the specification, persons skilled in the art should know that these embodiments are merely described by way of example, and persons skilled in the art may make various changes, improvements, and replacements without departing from the present invention. Therefore, the protection scope of the present invention should be defined in accordance with the spirit and scope of the appended claims of the present invention.

While particular embodiments are described above, it will be understood it is not intended to limit the invention to these particular embodiments. On the contrary, the invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

The invention claimed is:

1. A sealing ring protection sheet for a trocar comprising:
   one positioning skirt;
   one support piece; and
   one curved surface protection sheet, wherein:
   A. the positioning skirt is a sheet structure, and is provided with a positioning hole and an inner side of the positioning skirt is connected to an upper end of the support piece;
   B. the support piece is a sheet structure, and the upper end of the support piece is connected to the inner side of the positioning skirt and a lower end of the support piece is connected to an upper end of the curved surface protection sheet; and
   C. the curved surface protection sheet is an asymmetrical sheet structure having a curved surface and divided into a right side and a left side by a center line of the positioning skirt that splits the positioning hole evenly and extends through the curved surface protection sheet, the right side and the left side having different sizes, the right side further including a right bevel edge, a bottom edge, and the left side further including a left bevel edge, an upper edge, and a transition arc, and the right bevel edge and the left bevel edge are on both sides of the bottom edge, the curved surface protection sheet is suspended on the support piece, the upper edge of the curved surface protection sheet is connected to the lower end of the support piece.

2. The sealing ring protection sheet for a trocar according to claim 1, wherein: an included angle α between the curved surface protection sheet and the support piece is greater than or equal to 90°.

3. The sealing ring protection sheet for a trocar according to claim 1, wherein: an included angle β between the left bevel edge and the bottom edge is between 70° and 90°.

4. The sealing ring protection sheet for a trocar according to claim 1, wherein: the right bevel edge and the left bevel edge are asymmetrically distributed along the center line of the positioning skirt.

5. The sealing ring protection sheet for a trocar according to claim 4, wherein: a furthest distance between the right bevel edge and the center line of the positioning skirt is less than a furthest distance between the left bevel edge and the center line of the positioning skirt.

6. The sealing ring protection sheet for a trocar according to claim 1, wherein: the curved surface protection sheet used in the sealing ring protection sheet of the trocar is disposed with a deformable region and a protection region, and a deformation resistance force of the easily deformable region is less than a deformation resistance force of the protection region.

7. The sealing ring protection sheet for a trocar according to claim 6, wherein: the deformable region is disposed on the right side of the curved surface protection sheet of the sealing ring protection sheet for a trocar relative to the center line of the positioning skirt, and the protection region is disposed on the left side of the curved surface protection sheet of the sealing ring protection sheet relative to the center line of the positioning skirt.

8. The sealing ring protection sheet for a trocar according to claim 7, wherein: a thickness of the deformable region is less than a thickness of the protection region.

9. The sealing ring protection sheet for a trocar according to claim 1, wherein: a funnel-shaped protection sheet assembly is formed by alternately stacking four or more sealing ring protection sheets.

10. The sealing ring protection sheet for a trocar according to claim 9, wherein: the funnel-shaped protection sheet assembly is formed by alternately stacking eight sealing ring protection sheets at 45°, the eight sealing ring protection sheets including the four or more sealing ring protection sheets.

11. The sealing ring protection sheet for a trocar according to claim 1, wherein: a curvature of a left side portion of the curved surface protection sheet is different from that of a right side portion of the curved surface protection sheet.

12. The sealing ring protection sheet for a trocar according to claim 11, wherein: the curvature of the left side of the curved surface protection sheet is less than that of the right side of the curved surface protection sheet.

13. The sealing ring protection sheet for a trocar according to claim 1, wherein: the upper edge of the curved surface protection sheet comprises a right-side upper edge, a left-side upper edge; and the right-side upper edge is lower than the left-side upper edge.

14. The sealing ring protection sheet for a trocar according to claim 1, wherein: the positioning skirt is perpendicular to the support piece.

15. An end sealing assembly, wherein: the end sealing assembly comprises eight instances of the sealing ring protection sheet for a trocar according to claim 1.

16. The end sealing assembly according to claim 15, wherein: the end sealing assembly comprises an upper pressing plate, a corrugation sealing ring, a positioning seat, a funnel-shaped sealing ring and a lower pressing plate; the eight sealing ring protection sheets are mounted on positioning posts of the upper pressing plate through positioning holes, so that for any two adjacent sealing ring protection sheets, a right side of a curved surface protection sheet of one of the two adjacent sealing ring protection sheets always presses a left side of a curved surface protection sheet of the other one of the two adjacent protection sheets, the right side of the curved surface protection sheet of the one of the two adjacent sealing ring protection sheets is always in an upper layer, and the left side of the curved surface protection sheet of the other one of the two adjacent protection sheets is always in a lower layer, to thus form a circular funnel-shaped protection sheet assembly by alternately stacking the eight sealing ring protection sheets in this manner; positioning holes of the corrugation sealing ring are sleeved on the positioning posts of the upper pressing plate, and the circular funnel-shaped protection sheet assembly is disposed between the corrugation sealing ring and the upper pressing plate; the positioning seat is provided with upper positioning holes and lower positioning holes, the positioning posts of the upper pressing plate are embedded in the upper positioning holes of the positioning seat, and the eight sealing ring protection sheets and the corrugation sealing ring are sequentially disposed between the upper pressing plate and the positioning seat; and the funnel-shaped sealing ring is provided with positioning holes, the lower pressing plate is provided with positioning posts, the positioning posts of the lower pressing plate are embedded in the lower positioning holes of the positioning seat through the positioning holes of the funnel-shaped sealing ring, and the funnel-shaped sealing ring is disposed between the lower pressing plate and the positioning seat.

17. A trocar, wherein: the trocar comprises eight instances of the sealing ring protection sheet for a trocar according to claim 1.

18. The trocar according to claim 17, wherein: the trocar comprises an end sealing assembly, the end sealing assembly further comprising an upper pressing plate, a corrugation sealing ring, a positioning seat, a funnel-shaped sealing ring and a lower pressing plate; the eight sealing ring protection sheets are mounted on positioning posts of the upper pressing plate through positioning holes, so that for any two adjacent sealing ring protection sheets, a right side of a curved surface protection sheet of one of the two adjacent sealing ring protection sheets always presses a left side of a curved surface protection sheet of the other one of the two adjacent protection sheets, the right side of the curved surface protection sheet of the one of the two adjacent sealing ring protection sheets is always in an upper layer, and the left side of the curved surface protection sheet of the other one of the two adjacent protection sheets is always in a lower layer, to thus form a circular funnel-shaped protection sheet assembly by alternately stacking the eight sealing ring protection sheets in this manner; positioning holes of the corrugation sealing ring are sleeved on the positioning posts of the upper pressing plate, and the circular funnel-shaped protection sheet assembly is disposed between the corrugation sealing ring and the upper pressing plate; the positioning seat is provided with upper positioning holes and lower positioning holes, the positioning posts of the upper pressing plate are embedded in the upper positioning holes of the positioning seat, and the eight sealing ring protection sheets and the corrugation sealing ring are sequentially disposed between the upper pressing plate and the positioning seat; and the funnel-shaped sealing ring is provided with positioning holes, the lower pressing plate is provided with positioning posts, the positioning posts of the lower pressing plate are embedded in the lower positioning holes of the positioning seat through the positioning holes of the funnel-shaped sealing ring, and the funnel-shaped sealing ring is disposed between the lower pressing plate and the positioning seat.

* * * * *